United States Patent
Dion et al.

(10) Patent No.: US 6,742,236 B1
(45) Date of Patent: Jun. 1, 2004

(54) MAKING CLOSED END TUBES FOR SURGICAL INSTRUMENTS

(75) Inventors: Ernest A. Dion, Danvers, MA (US); Ronald A. Mayville, Newton, MA (US); Joop F. Hoekstra, Medfield, MA (US); John L. O'Brien, Winchester, MA (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 09/399,596

(22) Filed: Sep. 20, 1999

(51) Int. Cl.[7] .......................... B23P 11/00; A61B 17/32
(52) U.S. Cl. .......................... 29/434; 29/558; 606/171; 72/370.13
(58) Field of Search .................. 29/517, 557, 558, 29/434; 72/370.13, 370.12, 370.25, 370.02, 370.1, 356, 361, 352; 606/167, 170, 171

(56) References Cited

U.S. PATENT DOCUMENTS

| | | | | |
|---|---|---|---|---|
| 378,976 A | * | 3/1888 | Ritchie | 220/604 |
| 389,087 A | * | 9/1888 | Kennedy | 228/15.1 |
| 1,903,630 A | * | 4/1933 | Minor | 72/340 |
| 2,026,133 A | * | 12/1935 | Mapes | 72/377 |
| 2,069,858 A | * | 2/1937 | Squires | 72/479 |
| 2,284,210 A | * | 5/1942 | Johnson | 228/112.1 |
| 2,309,561 A | * | 1/1943 | Westin et al. | 219/149 |
| 2,325,522 A | * | 7/1943 | Lauer et al. | 72/318 |
| 2,421,629 A | * | 6/1947 | Langos | 72/370.12 |
| 3,695,087 A | * | 10/1972 | Tuberman | 72/402 |
| 4,361,948 A | * | 12/1982 | Omata | 29/517 |
| 4,598,710 A | | 7/1986 | Kleinberg et al. | 606/170 |
| 4,850,354 A | * | 7/1989 | McGurk-Burleson et al. | 606/170 |
| 5,217,479 A | * | 6/1993 | Shuler | 606/180 |
| 5,320,635 A | | 6/1994 | Smith | 606/180 |
| 5,676,012 A | | 10/1997 | Ceriale | 72/294 |
| 5,733,297 A | * | 3/1998 | Wang | 606/167 |
| 5,833,702 A | | 11/1998 | Van Wyk et al. | 606/167 |
| 5,843,106 A | | 12/1998 | Heisler | 606/167 |

FOREIGN PATENT DOCUMENTS

| | | |
|---|---|---|
| DE | 3313273 A | 10/1984 |
| DE | 3544753 A | 6/1987 |
| EP | 0 424 945 | 4/1997 |

* cited by examiner

Primary Examiner—Gregory Vidovich
Assistant Examiner—Marc Jimenez
(74) Attorney, Agent, or Firm—Fish & Richardson P.C.

(57) ABSTRACT

Techniques are described for making one-piece tubes for surgical instruments in which an inner tube that carries a cutting implement is disposed for movement within an outer tube having a cutting window that exposes the cutting implement to tissue. Swaging is performed to close an end of a tubular member that is to serve as either the inner tube or the outer tube. Other processing steps are also performed. For example, a selected amount of a protrusion formed by the swaging is cut away, the tube material is fused together at a seam formed by the swaging, and the closed distal end of the tubular member is formed into a selected shape. For example, the selected shape is rounded so that the distal end defines convex (e.g., substantially hemispherical) interior and exterior distal surfaces. This renders the tube suitable for use in full-radius surgical instruments. Alternatively, the selected shape is flattened so that the distal end defines flattened interior and exterior distal surfaces. In this case, the tube can be used in end cutting surgical instruments.

30 Claims, 9 Drawing Sheets

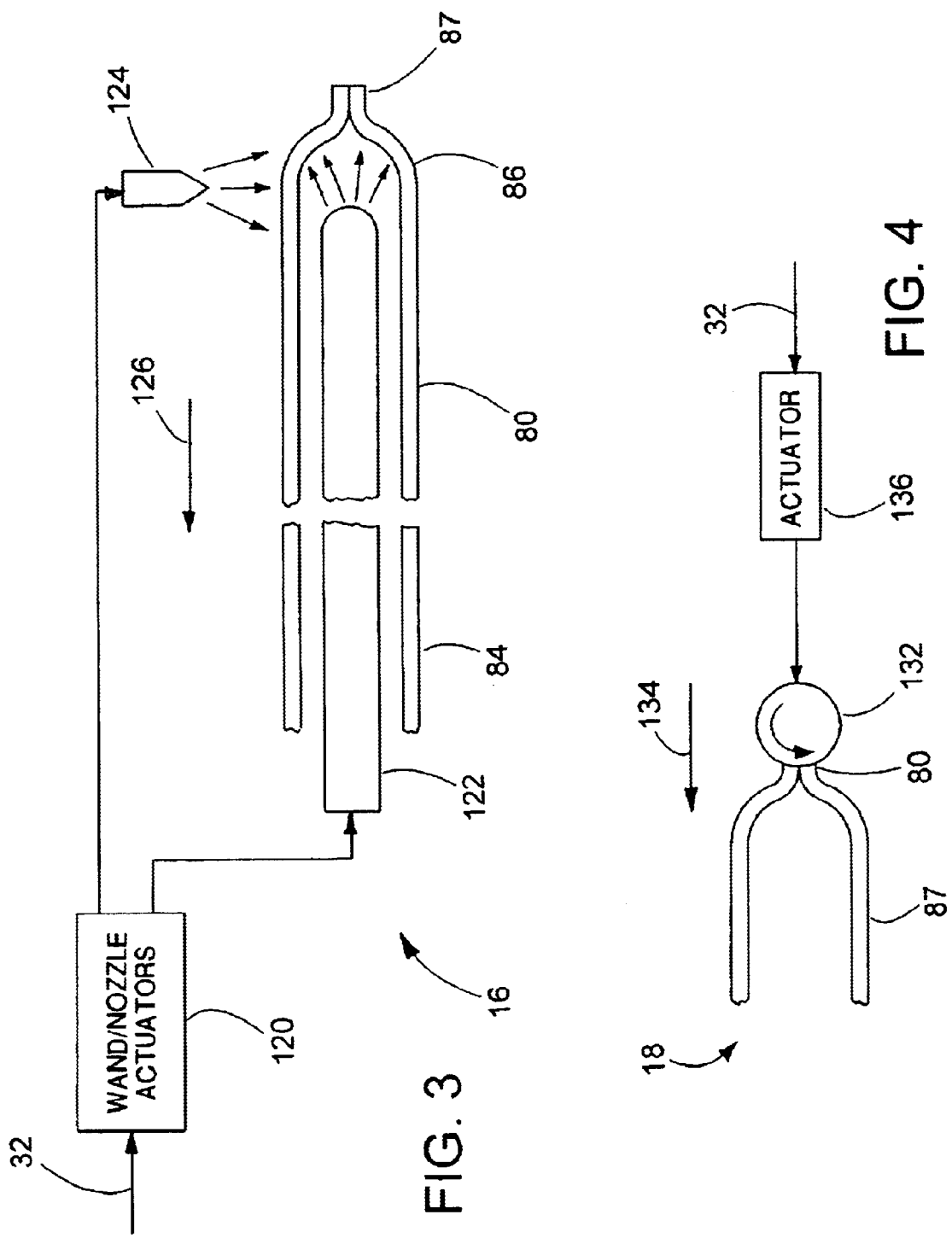

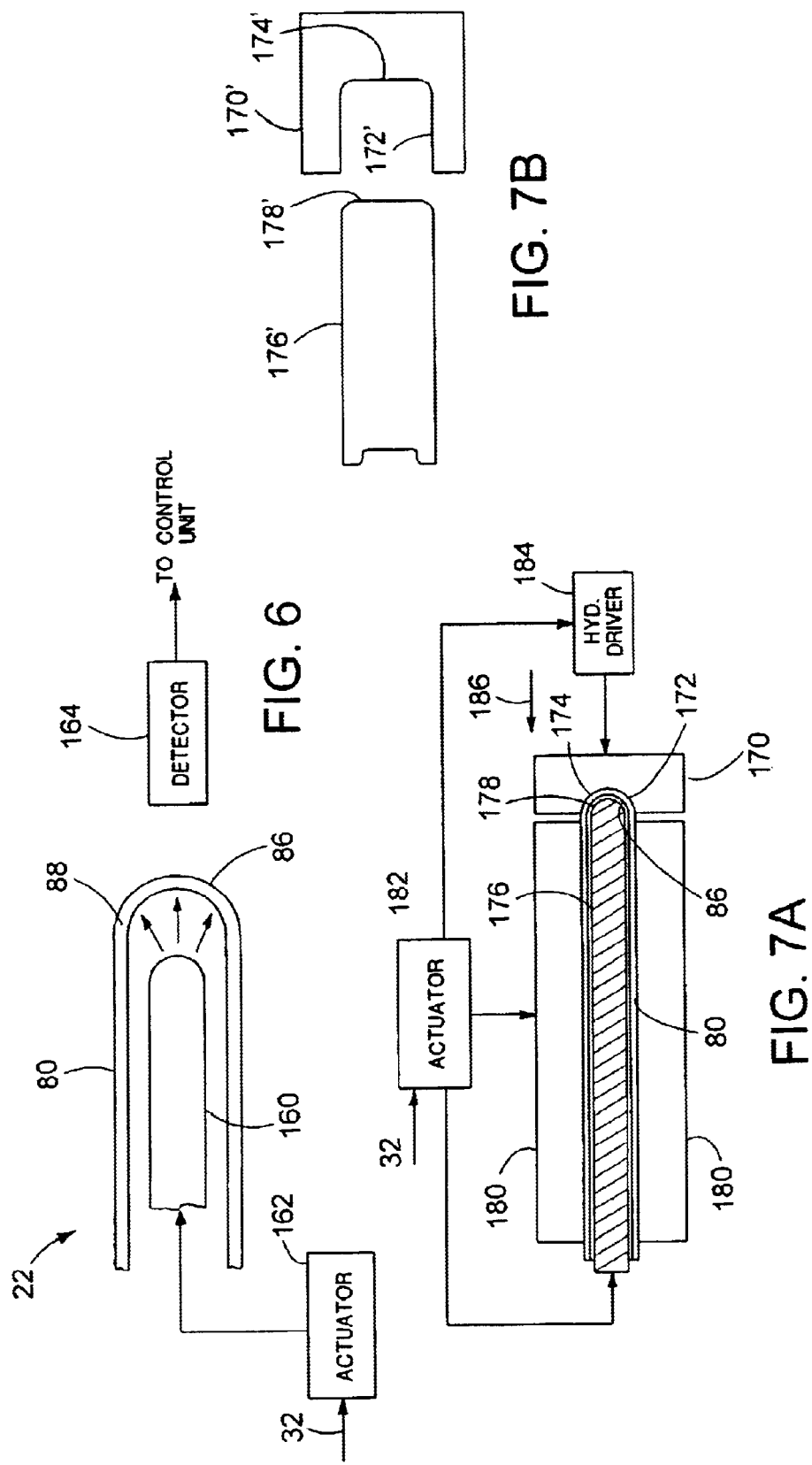

MAKING CLOSED END TUBES FOR SURGICAL INSTRUMENTS

BACKGROUND

This invention relates to making surgical instruments, in particular surgical instruments in which an inner tube that carries a cutting implement is disposed for movement within an outer tube having a cutting window that exposes the cutting implement to tissue.

The inner and outer tubes of such surgical instruments typically have closed distal ends, and the cutting implement and window are formed at or near the distal ends. The cutting implement is often an opening with sharpened edges, in which case the edges of the window may also be sharpened. In some cases, the cutting implement and window are formed in the closed distal ends themselves.

The tubes are typically made from two pieces—a metal tube open at both ends and a hollow, drawn metal tip which is open at one end and closed at the other. The open end of the tip is attached to one end (e.g., the distal end) of the tube, such as by plasma arc welding. The weld joint is smoothed by, e.g., centerless grinding.

One scheme for making the tube from one piece is known as "spinning." In this process, the open distal end of the tube is cut off at a shallow angle to produce an elongated, generally side-facing opening. The tube and a supporting mandrel are then spun at high speeds and advanced into a die. The friction between the tubs and the die heats the tube to a plastic state so that the die forces the material surrounding the opening to one side. This forms a rounded, closed end at the distal tip of the tube, and a side-facing opening located proximally of the tip.

SUMMARY

This invention features making a one-piece inner or outer tube for a surgical instrument by swaging the open end of the tube closed. Among other advantages, closing the tube by swaging reduces manufacturing complexity. For example, swaging eliminates several steps associated with the two-piece attachment process (e.g., straightening the two-piece tube and grinding smoothing the joint between the tip and the tube). Additionally, there is no need to cut an elongated opening in the tube, as in the spinning process.

In one general aspect of the invention, a tubular member that is to serve as either the inner tube or the outer tube is provided, and an open distal end of the tubular member is swaged closed.

Preferred embodiments may include one or more of the following features.

The swaging is performed by rotary swaging. The tubular member includes a distal edge that defines an opening at the distal end, the swaging driving regions of the tubular member disposed adjacent to the distal edge together to close the opening. Prior to swaging, the distal edge is disposed symmetrically about, and perpendicular to, an axis of the tubular member, and the swaging drives the adjacent regions of the tubular member together symmetrically with respect to the axis.

The swaging produces a seam in material of the tubular member at the distal end, and this material is fused together at the seam. Preferably, the fusion is performed by welding the distal end.

The swaging also produces a protrusion of the tubular member material at the seam. Prior to welding, a selected amount of the protrusion is cut away. Performing this step helps control the final tube length as well as the wall thickness at the distal end.

The closed distal end of the tubular member is formed into a selected shape. Preferably, this is done by pressing the distal end of the tube between a pair of dies that define the selected shape.

In one embodiment, the selected shape is rounded so that the distal end defines convex (e.g., substantially hemispherical) interior and exterior distal surfaces. This renders the tube suitable for use in full-radius surgical instruments. In another embodiment, the selected shape is flattened so that the distal end defines flattened interior and exterior distal surfaces. In this case, the tube can be used in end cutting surgical instruments.

The tubular member may be provided as the inner tube of the surgical instrument, in which case, a cutting implement is disposed at the distal end of the tubular member. The tubular member is disposed for rotation within the outer tube of the surgical instrument.

The tubular member may be provided as the outer tube of the surgical instrument, in which case a window is defined at the distal end for exposing a cutting implement carried by the inner tube.

A second tubular member may be provided to serve as the other one of the inner tube or the outer tube. Swaging is performed to close the open distal end of the second tubular member.

Another general aspect of the invention features performing some or all of the actions discussed above to make a tube for use as an inner or outer tube of the surgical instrument. That is, swaging is performed to close the open distal end of the tubular member, a selected amount of a protrusion formed by the swaging is cut away, the tube material is fused together at a seam formed by the swaging, and the closed distal end of the tubular member is formed into a selected shape.

In another aspect of the invention, the swaging, cutting, fusing, and forming operations are performed at various stations. In a preferred embodiment, devices convey the tubular member between the stations, and a controller controls the conveying and coordinates operation of the stations.

The invention provides one-piece tubes with precisely sized and shaped closed distal ends within tight tolerances. This allows the inner and outer tubes to be designed to have small clearances between them for increased cutting efficiency. In addition, the one-piece construction is stiffer than typical two-piece tubes, because there is no weld joint that requires smoothing by centerless grinding or the like. The high degree of stiffness maintains the close running fit around the entire circumference of the tubes' distal ends and at the extreme distal tips of the tubes, even if the tubes are subjected to large side loads during use.

Other features and advantages of the invention will be apparent from the following description, and from the claims.

DRAWINGS

FIG. 3 illustrates a cleaning station.

FIG. 4 depicts a trimming station.

FIG. 6 depicts an inspection station.

FIG. 7A illustrates a forming station which forms the closed end of the tube into a hemispherical shape.

FIG. 7B shows a forming station which forms the closed end of the tube into a flattened shape.

DETAILED DESCRIPTION

Figure 1:
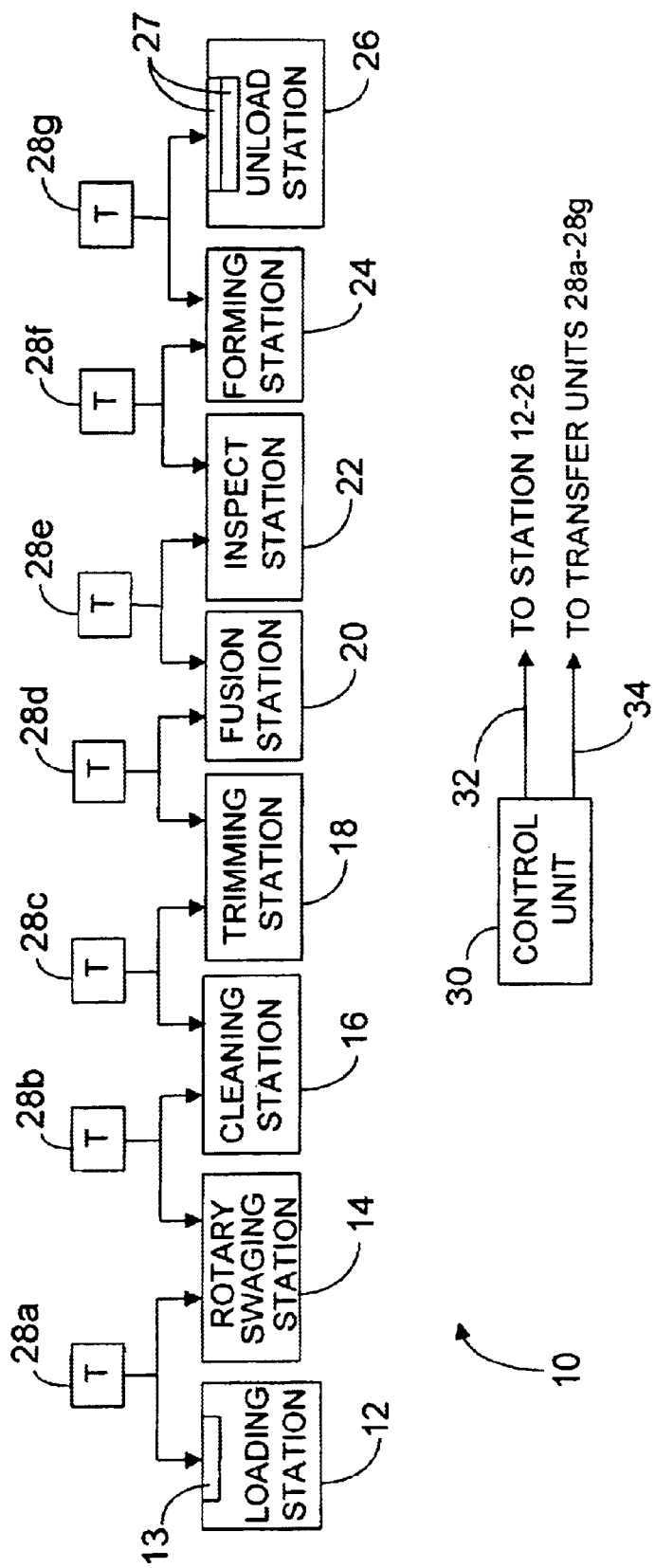
FIG. 1 is a block diagram of an assembly line of stations for manufacturing a tube of a surgical instrument.

FIG. 1 shows an assembly line 10 for manufacturing the inner and outer tubes of a surgical instrument from tube stock, e.g., tubular members open at both ends. Assembly line 10 includes stations 12–26 for performing various operations on the tube stock, described below, and transfer units 28a–28g which convey the tube stock between stations 12–26. A computerized control unit 30 controls the operation of stations 12–26 by issuing commands on bus 32, and coordinates this operation with the transfer of tube stock between stations 12–26 by sending control signals to transfer units 28a–28g via bus 34.

As will be explained below, by appropriately configuring stations 12–26, assembly line 10 can fashion the inner and outer tubes of surgical instruments having various cutting configurations (e.g., full radius resectors, end cutters, etc.) and sizes (e.g., nominal outer diameter of 4.5 mm, 5 mm, etc.). Typically, stations 12–26 are set up to produce a large production run (e.g., 1000) of tubes having a selected size and cutting configuration (e.g., 1000 inner tubes for a 4.5 mm full radius resector). Then, various stations 12–26 are reconfigured for a production run of differently configured or sized tubes.

The steps performed by stations 12–26 are described in detail below, but in general, assembly line 10 closes the distal end of each tubular member by rotary swaging, treats the closed distal end in various stages to prepare it for final shaping, and forms the closed distal end into a selected shape suitable for use in a surgical instrument. For example, if the tube stock is to become an inner or outer tube of a full-radius resector (such as the Sharp Full Radius and Incisor Plus blades manufactured by Smith & Nephew, Inc. of Andover, Mass.), the closed distal end is formed into a convex (e.g., hemispherical) shape. Alternatively, if the tube stock is to become an inner or outer tube of an end cutter (such as the RazorCutter and Cutter blades manufactured by Smith & Nephew, Inc.), the closed distal end is flattened in assembly line 10. Other shapes are, of course, possible.

The first station in assembly line 10 is loading station 12, which includes a hopper (not separately shown) capable of holding up to 1,000 pieces of tube stock. Prior to being placed in loading station 12, each tubular member in the tube stock is cut to the proper length. As discussed below, the correct tube stock length is important to the rotary swaging process. For the Smith & Nephew blades mentioned above, stock that will serve as inner tubes should have a length of 6.917 inches, while outer tube stock should be 5.693 inches in length. Tube stock for inner and outer tubes and tube stock for differently-configured (or differently-sized) surgical instruments are not mixed. That is, for a given production run in assembly line 10, the tube stock loaded into loading station 12 has a selected diameter and is precut to a length suitable for the kind of tube being fashioned in the production run.

Loading station 12 includes a measuring unit 13 that measures the length of each tubular member presented to it by the hopper. If the measurement is acceptable (e.g., within a tolerance of 0.005 inches), transfer unit 28a conveys the tubular member to the next station in assembly line 10, rotary swaging station 14. Otherwise, the tubular member is rejected and is dropped into a discard bin (not shown). For quality control purposes, if three consecutive tubular members are rejected, control unit 30 shuts down assembly line 10, as it is likely that the hopper has been loaded with the wrong-sized tubes.

Figure 2A:
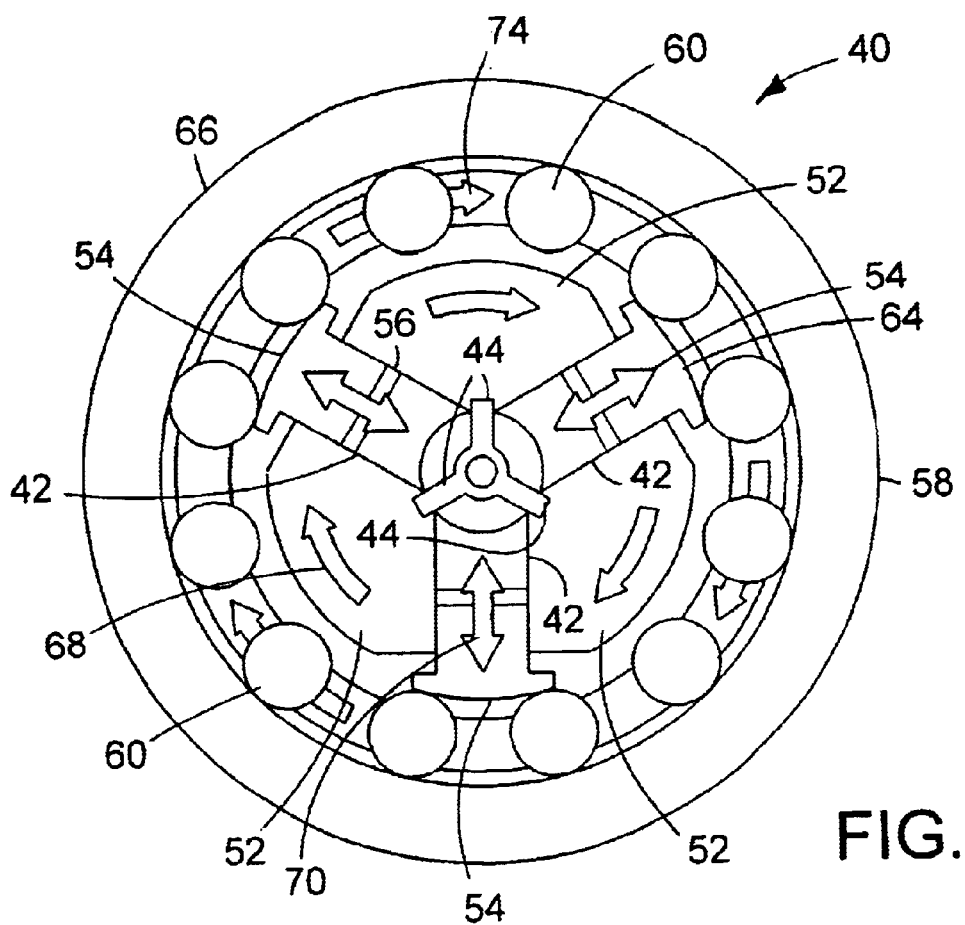
FIGS. 2A–2C show a rotary swaging station and some of the components of the station.
Figure 2B:
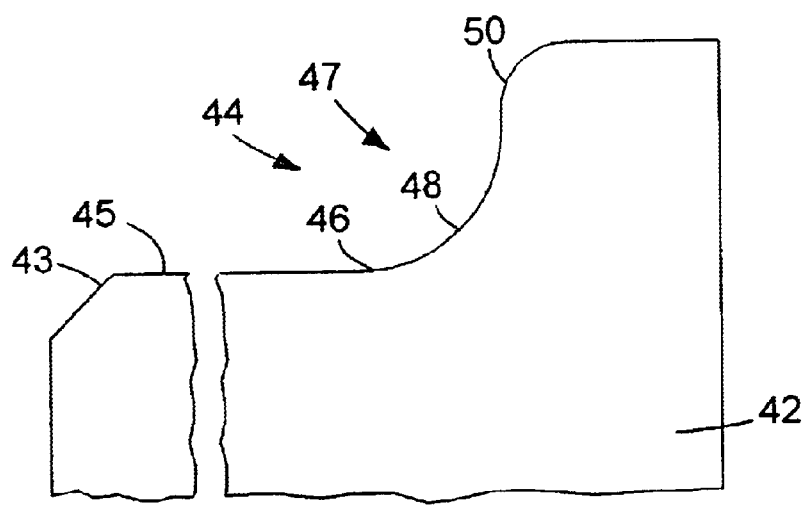
Figure 2C:
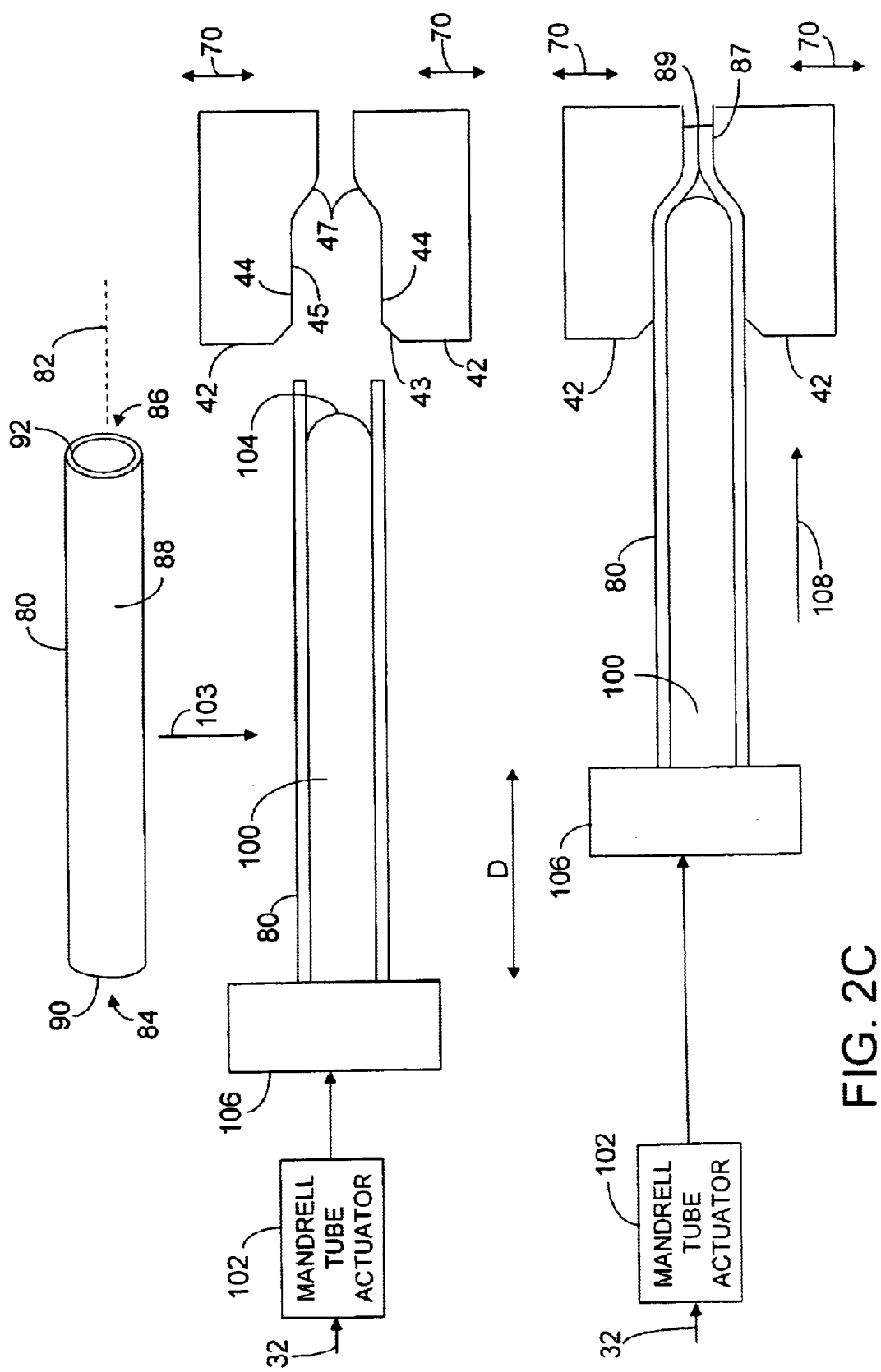

Referring to FIGS. 2A–2C, rotary swaging station 14 includes a rotary swager 40, model HE16D available from Gebr. Felss GmbH of Stein, Germany. Rotary swager 40 is equipped with three swaging die segments 42 spaced by 120 degrees from each other. Die segments 42 have identically shaped swaging surfaces 44, and are sized to correspond to the dimensions of the tube stock being processed. That is, differently-sized die segments 42 are used to swage tube stock that will serve as the inner and outer tubes, respectively, for each surgical instrument size (e.g., 4.5 mm, 5 mm, etc.). For a given size of tube stock, rotary swager 40 uses the same die segments 42 to produce tubes for full radius and end cutting instruments.

FIG. 2B is an enlarged cross-sectional view of a die segment 42 that shows the shape of swaging surface 44 in two dimensions. It will be understood, however, that swaging surfaces 44 are three dimensional, and are curved in the third dimension (i.e., cup-shaped) to accommodate the curved walls of the tube stock. Each swaging surface 44, viewed in cross-section, extends distally from an outwardly flared proximal region 43 through a straight intermediate region 45 to a generally S-shaped distal region 47. S-shaped distal region 47 extends axially from a relatively shallow concave leading end 46, through a more deeply concave intermediate region 48, and terminates in a convex trailing end 50.

Die segments 42 are disposed in radial guide slots between three sections 52 of a swaging shaft head. A thrust piece 54 and a shim 56 are positioned radially exteriorly of each die segment 42 in the guide slot. The swaging shaft head is surrounded by a roller cage 58 that includes a series of circumferentially spaced rollers 60, which are engaged by beveled end surfaces 64 of thrust pieces 54 in a manner to be described. Roller cage 58 is housed within an outer ring 66.

Rotary swager 40 is a so-called internal rotor machine. That is, during swaging, the swaging shaft head is rotated (in the direction of arrows 68) while outer ring 66 remains stationary. The centrifugal force applied to die segments 42 by the rotating swaging shaft head urges the die segments radially outwardly. Die segments 42 will be maximally opened when thrust pieces 54 are positioned between rollers 60. As thrust pieces 54 rotate into engagement with rollers 60, they are forced radially inwardly, thereby driving die segments 42 together. Die segments 42 are fully closed (although a small space remains between them at trailing ends 50) when thrust pieces 54 are centered beneath rollers 60. Thus, die segments 42 oscillate radially in the direction of arrows 70 during rotation of the swaging shaft head. Roller cage 58 is also mounted for rotation within outer ring 66, and thus the rotation of the swaging shaft head also induces roller cage 58 to rotate, as shown by arrows 74.

Referring to FIG. 2C, before discussing the operation of rotary swaging station 14, we briefly describe the construction of a tubular member 80 received from loading station 12. Tubular member 80 is made from 304L stainless steel and extends along a longitudinal axis 82 between an open proximal end 84 and an open distal end 86. The walls 88 of tubular member 80 are cylindrical and terminate at respective annular proximal and distal edges 90, 92, which are disposed symmetrically around, and are oriented perpendicularly to, axis 82. Thus, the openings at proximal and distal ends 84, 86 are in a plane arranged perpendicularly to axis 82.

Rotary swaging station 14 includes a mandrel and tube actuating mechanism 102 which operates an advancement assembly 106 in response to commands received from control unit 30 on bus 32 to feed tubular member 80 into rotary swager 40. Control unit 30 also manages the operation of swager 40, although the connection to bus 32 is not shown. After tubular member 80 has been loaded into rotary swaging station 14 (as represented by arrow 103), actuator 102 advances a mandrel 100 into tubular member 80 until a rounded distal end 104 of mandrel 100 is positioned slightly proximally of tubular member distal end 86. Control unit 30 activates rotary swager 40 to radially oscillate die segments 42 (as shown by arrows 70), and directs actuator 102 to cause advancement assembly 106 to axially advance mandrel 100 and tubular member 80 together into rotary swager 40 (along arrow 108).

The tapered proximal regions 43 of die segments 42 help ensure that distal end 86 of tubular member 80 is not damaged as it enters swager 40. The intermediate regions 45 of die segments 42 used during the fabrication of inner tubes are sized so that when die segments 42 are fully closed, intermediate regions 45 define a passage that is slightly larger than the outer diameter of tubular member 80. As a result, intermediate regions do not swage distal end 68 as it is advanced toward S-shaped region 47.

In contrast, when swager 40 is set up to swage tubular members 80 to form outer tubes, the die segments 42 that are used have intermediate regions 45 sized to define a passage slightly smaller than the outer diameter of tubular member 80 when die segments 42 are closed. As a result, as the distal regions of these tubular members are advanced into rotary swager 40, die segment intermediate regions 45 repeatedly hammer against walls 88 to drive or "peen" walls 88 symmetrically inwardly, thereby narrowing tubular member 80. As a result, the outer and inner diameters of walls 88 are decreased so that the distal region of the outer tube will fit more closely against the inner tube (for increased cutting efficiency) than more proximal regions of the outer tube.

The rotary swaging process operates to close the distal ends of a tubular member (for either an inner tube or an outer tube) as follows. As tubular member 80 is advanced between S-shaped distal regions 47 of die segments 42, swaging surfaces 46, 48, 50 repeatedly hammer against regions of walls 88 located proximally adjacent to distal edge 92 to peen those regions of wall 88 together symmetrically with respect to axis 82. This "cold working" hardens the tube material somewhat. During swaging, injectors (not shown) continuously direct oil between tubular member 80 and die segments 42. The oil helps avoid seizure of die segments 42 and resulting damage to the swaged tubular member. One suitable oil is Twin-Draw #244, commercially available from Twin Specialties Corp. of Conshohocken, Pa. Mandrel 100 radially supports proximally adjacent regions of tubular member 80 during swaging to help prevent deformation in response to the large forces applied by die segments 42. Rounded distal end 104 of mandrel 100 ensures that the swaged regions of wall 88 assume a rounded shape for ease of subsequent fabrication.

Swaging continues as tubular member 80 is advanced between die segments 42, with the portions 48 of swaging surfaces 44 driving walls 88 more closely together as walls 88 extend distally. When tubular member 80 has been fully advanced into rotary swager 40, trailing ends 50 of swaging surfaces 44 force walls 88 together, thereby closing distal end 86 and forming a nipple 87 of compressed wall material that extends to distal edge 92. Although a seam 89 is formed between the interior surfaces of walls 88 at nipple 87, seam 89 is airtight, and thus distal end 86 is fully closed.

Figure 2D:
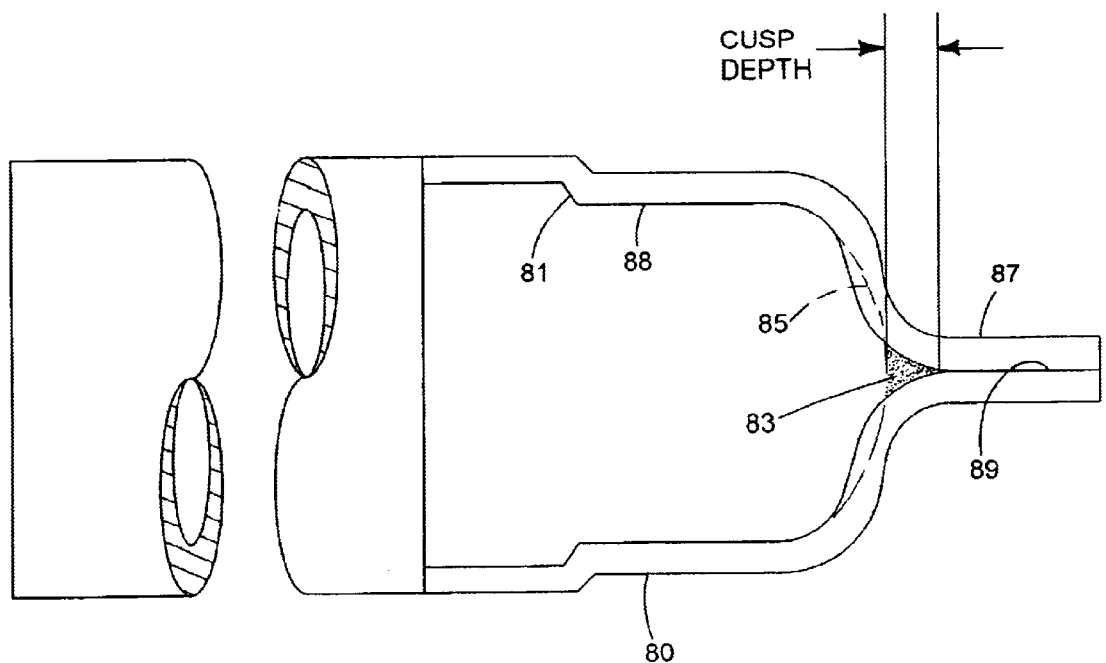
FIG. 2D shows the end of a tube that has been closed by the rotary swaging station.

FIG. 2D shows closed distal end 86 of a tubular member 80 for an outer tube in detail. (Note the annular transition 81 between the distal region of member 80, which has been swaged to a narrowed configuration, as described above, and the remainder of member 80.) At closed distal end 86, the interior surfaces of walls 88 form a cusp 83 proximally of seam 89 at nipple 87. The depth of cusp 83 is the distance between the point where walls 88 meet at seam 89 and an imaginary curve 85 that represents a hemispherical shape of distal end 86. If the cusp depth is too shallow, wall 88 will be too thick (even after trimming at station 18), and it will be difficult for forming station 24 to form closed end 86 into the desired final shape. In contrast, if the cusp is too deep, wall 88 will be too thin after trimming, and thus holes may be formed in closed end 86 during fusion (at station 20). Using 4.5 mm sized instruments as an example, we have found that the cusp depth should be 0.0138 inches for tubular members 80 that are being formed as outer tubes, and should be 0.0014 inches for tubular members 80 that are being formed as inner tubes.

The cusp depth is inversely related to the distance (called the stroke distance D, FIG. 2C) that actuator 102 advances tubular member 80 into rotary swager 40. If stroke distance D is too long, too much of tubular member 80 will be advanced between trailing surfaces 50 of die segments 42, and cusp 83 will be too shallow. In contrast, if stroke distance D is not long enough, an insufficient length of tubular member 80 will reach trailing surfaces 50, and hence cusp 83 will be too deep. Stroke distance D also affects the overall length of tubular member 80 that remains after nipple 87 is trimmed (at trimming station 18). That is, if stroke distance D is too long, nipple 87 will also be too long, and thus when trimmed tubular member 80 will be too short. On the other hand, if stroke distance D is not long enough, nipple 87 will be too small, and, even after the trimming and forming steps described below, tubular member 80 will be too long for the surgical instrument.

When swaging is complete, actuator 102 reverses the operation of advancement assembly 106 to withdraw tubular member 80 from rotary swager 40, and removes mandrel 100 from the tubular member. Next, transfer unit 28b conveys tubular member 80 to cleaning station 16 (FIG. 1).

Referring to FIG. 3, cleaning station 16 injects compressed air against the interior and exterior surfaces of tubular member 80 to remove residual lubricating oil applied at rotary swaging station 14. In response to control unit 30 commands sent via bus 32, actuators 120 advance an air wand 122 into tubular member 80 adjacent to closed distal end 86, and position an air nozzle 124 adjacent to the exterior surface of tubular member 80 near distal end 86. Air wand 122 and nozzle 124 inject compressed air (e.g., at 60 psi) against the interior and exterior surfaces, while simultaneously actuators 120 retract wand 122 and nozzle 124 proximally (in the direction of arrow 126). The compressed air blows excess oil proximally along the interior and exterior surfaces to proximal end 84 of tubular member 80, where the oil is collected by a vacuum collection system (not shown).

Referring to FIG. 4, when cleaning is complete, transfer unit 28c carries tubular member 80 to trimming station 130, where nipple 87 is ground down to remove excess tube material. The trimming step helps control the overall length of tubular member 80 and the wall thickness of closed distal end 86 after final shaping by forming station 24 (FIG. 1).

In response to commands from control unit 30, tubular member 130 is locked into position at trimming station 130 (by a clamp, not shown), and an actuator 136 proximally advances an abrasive cutting wheel 132 (in the direction of arrow 134) into contact with nipple 87. Cutting wheel 132 is rotated at high speed, and grinds away a substantial portion of nipple 87 as actuator 136 continues to advance wheel 132 further proximally along arrow 134. Actuator 136 advances wheel 132 a predetermined distance, and then retracts wheel 132. This distance is different for inner and outer tubes and is selected so that, if stroke distance D (FIG. 2C) is properly set so that tubular member 80 has the correct length, the wall thickness at nipple 87 remaining after wheel 132 is retracted is between 0.008 inch and 0.010 inch. When nipple 87 has been trimmed, control unit 30 directs actuator 136 to retract wheel 132, and triggers transfer unit 28d (FIG. 1) to convey tubular member 80 to fusion station 20.

Figure 5:
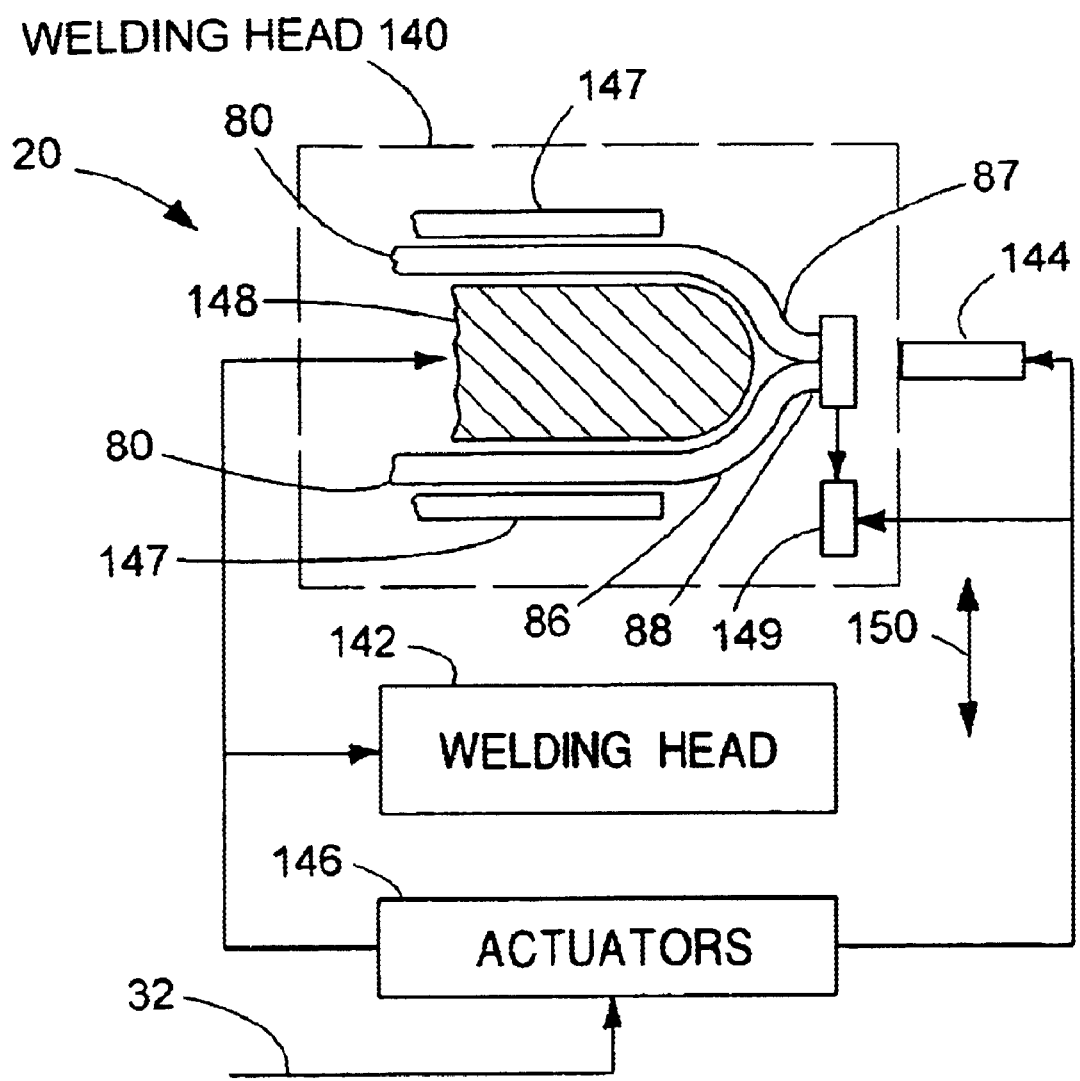
FIG. 5 shows a fusing station.

Referring to FIG. 5, fusion station 20 fuses walls 88 surrounding seam 89 together by welding, thereby eliminating seam 89 and forming a single, unitary structure at the extreme distal tip of closed end 86. In addition, the fusion process rounds off the distal tip of close end 86, and helps eliminate any laps, folds, or other structural defects in the swaged regions of walls 88. The welding process anneals the tip, thereby reducing the hardness of the material somewhat. As described below, however, the tip material is hardened again at forming station 24.

Fusion station 20 includes a pair of plasma arc welding heads 140, 142, which alternately receive tubular members 80, as described below. Fusion station 20 also includes a single weld torch 144, and actuators 146 that operate welding heads 140, 142 and weld torch 144 as described below in response to commands received from control unit 30.

Welding heads 140, 142 are identical, and thus only welding head 140 is shown in detail. Each welding head 140, 142 includes a collet 147 and a weld mandrel 148 sized to correspond to a specific tubular member size. That is, different pairs of collets 147 and mandrels 148 are loaded into welding heads 140, 142 for manufacturing inner and outer tubes, and for manufacturing tubes for different-sized instruments. Weld mandrel 148 is made from bronze, for example, a C-2 alloy of copper and chromium (CDA 18200, in RWMA group A, class 2, with a Rockwell hardness of at least 65B). Each welding head 140, 142 also includes a stop 149 for properly positioning tubular member 80 with respect to weld torch 144.

When a tubular member 80 is loaded into one of the welding units 140, 142, transfer unit 28d places tubular member 80 into collet 147. Actuators 146 advance weld mandrel 148 through tubular member 80 until the distal tip of mandrel 148 contacts the interior surface of walls 88 at closed distal end 86 and pushes nipple 87 against stop 149 (which is in the position shown in phantom in FIG. 5). Actuators then close collet 147 around tubular member 80, thereby securely clamping it in position, and withdraw stop 149 to expose nipple 87 to weld torch 144. (Although collet 147 is shown on only two sides of tubular member 80 in FIG. 5, it will be understood that collet 146 completely surrounds the exterior surface of tubular member 80 when closed.)

Next, actuators 146 advance weld torch 144 into contact with distal end 86 at nipple 87 and activate torch 144. The electrical current between weld torch 144, weld mandrel 148, and tubular member 80 heats the material of walls 88 at nipple 87 into a molten state, thereby fusing the material together at the distal tip of closed distal end 86, and eliminating seam 89. Mandrel 148, which has a rounded distal tip, serves as a heat sink to help prevent damage to distal end 86, and also helps control the flow of the molten wall material so that it assumes the rounded shape of the mandrel distal tip. To help ensure that the distal tip of tubular member 80 is uniformly fused, actuators 146 rotate collet 147 (and hence tubular member 80), e.g., at 100 rpm during the time that torch 144 is activated. When welding is complete, actuators 146 retract welding torch 144 and weld head 148 and open collet 147 to allow transfer unit 28e (FIG. 1) to grasp tubular member 80 and convey it to inspection station 22.

Control unit 30 synchronizes the operation of welding heads 140, 142, weld torch 144, and transfer units 28d, 28e. For example, while a tubular member 80 is being welded in welding head 140, control unit 20 directs transfer unit 28d to load a second tubular member in welding head 142. When weld torch 144 has finished at welding head 140, control unit 30 commands actuators 146 to move weld torch 144 into position for welding at welding head 142 (as shown by arrow 150), triggers transfer unit 28e to convey the completed tubular member 80 from welding head 140 to inspection station 22, and directs transfer unit 28d to load another tubular member 80 into welding head 140. Control unit 30 repeats this process after weld torch 144 has completed welding tubular member 80 in welding head 142.

The fusion process is performed in the same way for the various sizes of tubular members 80 and types of tubes (hemispherical, flat-ended) being fabricated. Because tubular members 80 being formed as inner tubes are smaller than members 80 for outer tubes, actuators 146 control weld torch 144 to apply smaller electrical currents during fusion of tubular members 80 for inner tubes.

Referring to FIG. 6, at inspection station 22, an inspection device 160, such as a high power light source, is advanced an actuator 162 through tubular member 80 to closed distal end 86 and activated, all under the control of control unit 32. A detector 164 senses whether any light emitted by the light source shines through walls 88, and reports the results control unit 30. The detection of light from the light source means that a blow hole or other opening is present in distal end 86 (caused, e.g., by burn-back during welding at fusion station 22 if the walls of distal end 86 at nipple 87 are too thin). Control unit 30 directs transfer unit 28f to remove such a defective tubular member 80 from assembly line 10 and place it in a reject hopper (not shown). On the other hand, if light is not sensed by detector 164, control unit 30 triggers transfer unit 28f to convey tubular member 80 to forming station 24.

FIG. 7A shows forming station 24 set up to form distal end 86 into a hemispherical shape suitable for an inner or outer tube of a full radius resector. The hemispherical shape is provided by a die 170, the outer surface 172 of which defines a hemispherical recess 174, and a mandrel 176 having a complementary-shaped distal end 178. (The arrangement of forming station 24 for manufacturing inner or outer tubes with flattened distal ends for end cutting instruments is discussed below.) Die 170 is made from carbide material (e.g., 82% tungsten carbide with 18% cobalt binder) having an 87.5 (RWA) hardness and a transverse rupture strength of 448,000 pounds/square inch. Mandrel 176 is made from M2 tool steel and has a hardness of 61–63 Rockwell C. Mandrel 176 is coated with a one micron thick layer of titanium nitrate to reduce surface friction between the mandrel and distal end 86 and thereby avoid galling or cold welding.

Transfer unit 28f loads tubular member 80 into a clamp 180, which extends along the entire length of tubular member 80 to support it during the forming process. (Although clamp 180 is shown on only two sides of tubular member 80, it will be understood that clamp 180 completely surrounds the exterior surface of tubular member 80.)

Forming station 24 operates as follows in response to the commands issued by control unit 30 over bus 32. First, actuators 182 close clamp 180 tightly around tubular member 80, and then pneumatically advance mandrel 176 through tubular member 80 until the mandrel distal end 178 is positioned adjacent to, but closely spaced from (e.g., by 0.1 inch), the interior surface of closed distal end 86 of tubular member 80. The pneumatic advancement rapidly positions mandrel 176 to reduce the overall time of the forming cycle.

Actuators 182 then signal a hydraulic driver 184 to hammer die 170 against the clamped distal end 86 of tubular member 80 (in the direction of arrow 186). This action compresses distal end 86 between recessed surface 172 and mandrel distal end 178 (which serves as a second die), thereby forming distal end 86 into the hemispherical shape. To ensure that distal end 86 is fully shaped, actuators 182 direct hydraulic driver 184 to slightly retract die 170 away from tubular member 80, and then repeat the hammering step. When the forming process has been completed, actuators 182 retract mandrel 176 and release clamp 180.

Because distal end 86 has a predetermined wall thickness (provided, as discussed above, by the parameters of the rotary swaging and trimming steps), when subjected to the forming process a sufficient amount of tube material is displaced to both achieve the final shape (in this example, hemispherical) and to reduce the thickness of walls 88 sufficiently to increase the hardness of distal end 86. That is, the cold working provided by the forming process forces the grain boundaries of the wall material to rub against each other, thereby thinning the wall and increasing its hardness. Thus, it is seen that in assembly line 10, the hardness of the material of distal end 86 is first increased (in rotary swaging station 14), decreased (in fusion station 20), and finally increased again (in forming station 24). The resulting hardness of distal end 86 after forming is preferably in the range of 210 Vickers–390 Vickers (e.g., 254 Vickers, or 23 Rockwell C).

Figure 8A:
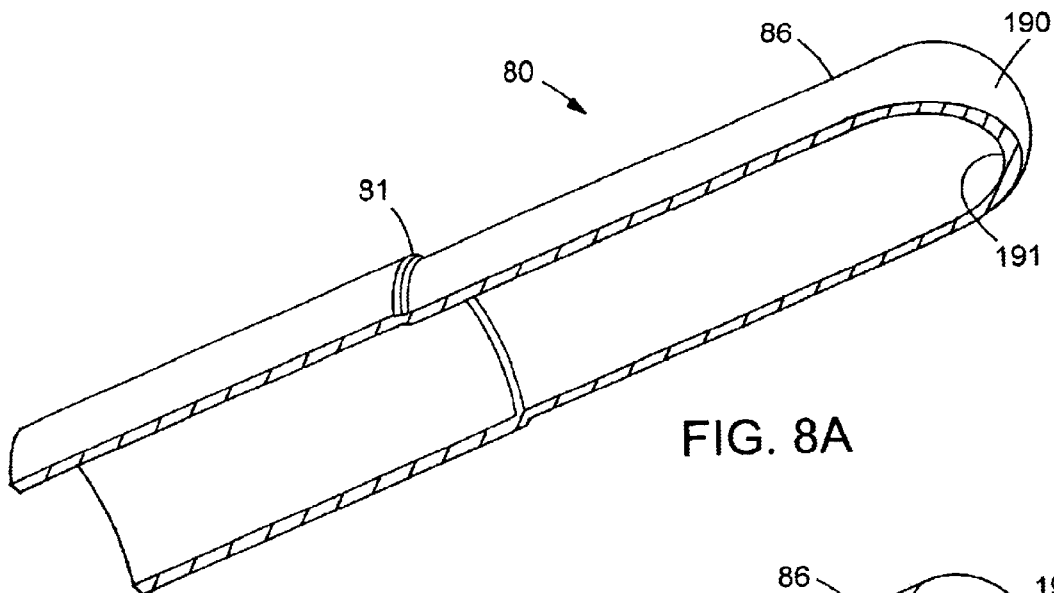
FIG. 8A shows such a formed tube, partially cut away.

Referring to FIG. 8A, at this point, manufacture of tubular member 80 in assembly line 10 is complete. The distal end 86 of tubular member 80 has been rounded to define a hemispherical exterior distal surface 190 and a corresponding hemispherical interior distal surface 191 suitable for use in a full radius resector. (FIG. 8A also shows the swaged transition 81 discussed above.) Control unit 30 instructs transfer unit 28g to remove tubular member 80 from clamp 180 and convey tubular member 80 to unload station 26.

Figure 8B:
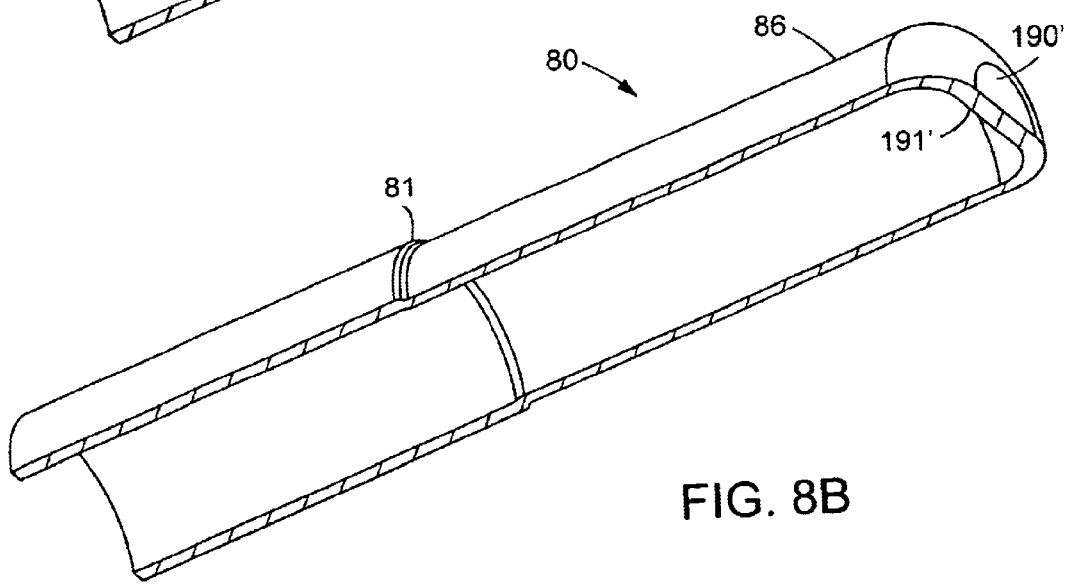
FIG. 8B shows such a formed tube, partially cut away.

Referring to FIGS. 7B and 8B, if tubular member 80 is to become an inner or outer tube of an end-cutter, die 170' and mandrel 176' are used in forming station 24 in place of hemispherical die 170 and mandrel 176. The outer surface 172' of die 170' defines a recess 174' with a flattened bottom surface and cylindrical side surfaces that meet the bottom surface at a rounded annular corner. The distal end 178' of mandrel 176' is complementary to the flattened shape of recess 174'. (The die and mandrel materials are the same as those discussed above for the hemispherical die and mandrel.) Forming station 24 is used in the same way as discussed above, and as a result, die 170' and mandrel 176' flatten distal end 86 of tubular member 80 to define a flattened exterior distal surface 190' and a corresponding flattened interior distal surface 191' suitable for use in, e.g., an end cutting instrument.

Die recesses 174, 174' and mandrels 176, 176' are sized differently according to whether the inner or outer tube of a given size (e.g., a 5.5 mm) instrument is being formed from tubular member 80. In addition, other sets of dies (not shown) are used to manufacture the inner and outer tubes for instruments having other sizes (e.g., 4.5 mm).

Unload station 26 (FIG. 1) includes a pair of storage trays 27 loaded with the finished tubular members 80 by transfer unit 28g. When one tray 27 is full, control unit 30 signals the operator to replace it, and triggers transfer unit 28g to load tubular members 80 into the other tray 27. The unloaded tubular members 80 then undergo further manufacturing (not shown) to fashion them as the inner and outer tubes of a surgical instrument.

For example, appropriately-configured windows are formed in distal ends 86 of tubular members 80, and the edges of the windows are sharpened (with either smooth or serrated surfaces) to form tissue cutting implements. Proximal ends 84 of tubular members 80 are secured to plastic hub components to enable the surgical instrument to be received and operated by a motorized handpiece (not shown). Tubular members 80 that will become outer tubes of the surgical instruments are swaged in their distal regions to reduce their inner diameters and achieve a close running fit with the inner tubes.

Figures 9A, 9B:
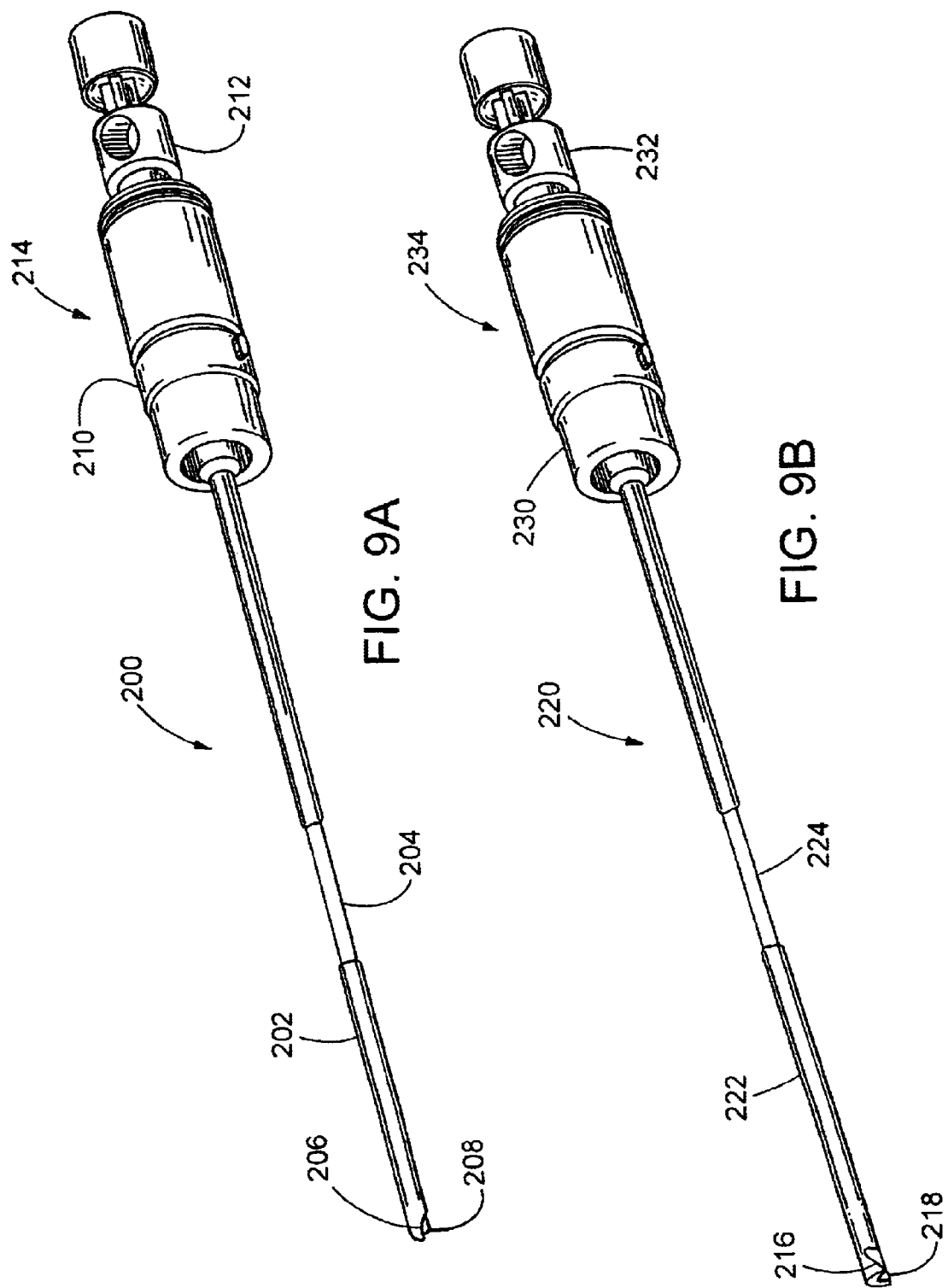
FIGS. 9A and 9B illustrate surgical instruments having tubes made by the assembly line of FIG. 1.

FIG. 9A shows a full-radius resector 200 having an outer tube 202 and an inner tube 204 each of which are made from tubular members 80 produced by assembly line 10. Tubes 202, 204 have respective cutting implements 206, 208 (in this case, windows with smooth, sharpened edges) at their distal ends. The proximal ends of outer and inner tubes 202, 204 are respectively secured to a stationary component 210 and a rotatable component 212 of a plastic hub 214.

FIG. 9B shows an end cutter 220 with outer and inner tubes 222, 224 made from tubular members 80 produced by assembly line 10. Respective cutting implements 216, 218 are formed at the distal ends of tubes 222, 224, and the proximal ends of tubes 222, 224 are secured to plastic components 230, 232, respectively, of hub 234.

The use of instruments 200, 220 with the motorized handpiece during surgery is known, but will briefly be described, using instrument 200 as an example. Hub 214 is inserted into the handpiece so that stationary hub component 210 is securely attached thereto to engage rotatable hub component 212 with the handpiece motor. When the motor is activated, it rotates inner tube 204 within outer tube 202 at high speed (e.g., up to 5,000 rpm) so that cutting implements 206, 208 sever body tissue admitted through the outer tube window. The severed tissue fragments are removed by suction through inner tube 204.

The fabrication steps performed by assembly line 10 provide one-piece tubular members 80 with precisely shaped closed distal ends 190, 190' that accommodate the high rotational speeds achieved by instruments 200, 220. Making the tubes out of one piece eliminates the need to attach a formed distal end to an open-ended tube, thereby simplifying manufacture. In addition, the one-piece construction is stiffer than typical two-piece tubes, because there is no weld joint that requires smoothing by centerless grinding or the like. The high degree of stiffness maintains the close running fit around the entire circumference of the tubes distal ends and at the extreme distal tips of the tubes, even if the tubes are subjected to large side loads during use.

Other embodiments are within the scope of the following claims.

For example, other kinds of swagers, such as external rotor rotary swagers, may be used.

Inspection station 22 may employ other types of inspection devices and detectors. For example, the inspection device may inject compressed air at the closed distal end, and the detector positioned to sense the pressure of the injected air and thus detect the presence of holes in the tube walls.

Other types of fusion processes may be used. For example, different welding techniques (such as tig welding, laser beam welding, or resistance welding) may be performed in place of plasma arc welding.

Assembly line 10 can include other suitable stations, such as inspection stations at other stages of the line.

Assembly line 10 may be used to form tubes having other distal end configurations.

What is claimed is:

1. A method of making a surgical instrument of the kind that includes an inner tube disposed for movement within an outer tube, comprising
    providing a tubular member adapted to serve as one of the inner tube or the outer tube, the tubular member having an open distal end,
    rotary swaging the distal end of the tubular member closed, and
    forming the closed distal end to a shape that substantially matches a shape of another one of the inner tube or the outer tube,
    wherein portions of the tubes are adapted to interact with each other to perform a surgical operation in response to the movement of the inner tube within the outer tube,
    wherein the swaging produces a seam in material of the tubular member at the distal end, and further comprising cutting the material together at the seam, and
    wherein the swaging produces a protrusion of the tubular member material at the seam, and further comprising cutting away a selected amount of the protrusion prior to performing the fusing.

2. The method of claim 1 wherein the tubular member includes a distal edge that defines an opening at the distal end, the swaging comprising driving regions of the tubular member disposed adjacent to the distal edge together to close the opening.

3. The method of claim 2 wherein, prior to the swaging, the distal edge is disposed symmetrically about an axis of the tubular member, the swaging comprising driving the adjacent regions of the tubular member together symmetrically with respect to the axis.

4. The method of claim 2 wherein, prior to the swaying, the distal edge is disposed perpendicularly to the axis of the tubular member.

5. The method of claim 1 further comprising performing the fusing by welding the distal end.

6. The method of claim 1 further comprising forming the closed distal end of the tubular member into a selected shape.

7. The method of claim 6 wherein the selected shape is rounded so that the distal end defines convex interior and exterior distal surfaces.

8. The method of claim 7 wherein the convex distal surfaces are substantially hemispherical.

9. The method of claim 6 further comprising performing said forming by pressing the distal end between a pair of dies that define the selected shape.

10. The method of claim 1 further comprising
    providing the tubular member as the inner tube of the surgical instrument, and
    after the swaging, disposing a cutting implement at the distal end of the tubular member.

11. The method of claim 6 further comprising disposing the tubular member for rotation within the outer tube of the surgical instrument.

12. The method of claim 1 further comprising
    providing the tubular member as the outer tube of the surgical instrument, and
    after the swaging, defining a window at the distal end for exposing a cutting implement carried by the inner tube.

13. The method of claim 1 further comprising
    providing a second tubular member to serve as the other one of the inner tube or the outer tube, the second tubular member having an open distal end, and
    swaging the distal end of the second tubular member closed.

14. The method of claim 1, wherein the movement is coaxial rotation.

15. A method of making a surgical instrument of the kind that includes an inner tube having a closed distal end disposed for movement within an outer tube having a closed distal end, comprising
    providing a tubular member to serve as either the inner tube or the outer tube, the tubular member having an open distal end,
    swaging the distal end of the tubular member closed, the swaging producing a seam in material of the tubular member at the distal end and a protrusion of the tubular member material at the seam,
    cutting away a selected amount of the protrusion,
    fusing the material together at the seam after the cutting, and
    after the fusing, forming the closed distal end of the tubular member into a selected shape that substantially matches a shape of another one of the inner tube or the outer tube,
    wherein portions of the tubes are adapted to interact with each other to perform a surgical operation in response to the movement of the inner tube within the outer tube.

16. The method of claim 15 further comprising performing the swaging by rotary swaging.

17. The method of claim 15 further comprising performing the fusing by welding the distal end.

18. The method of claim 15 wherein the selected shape is rounded so that the distal end defines convex interior and exterior distal surfaces.

19. The method of claim 18 wherein the convex distal surfaces are substantially hemispherical.

20. The method of claim 15 wherein the selected shape is flattened so that the distal end defines flattened interior distal surfaces.

21. The method of claim 15 further comprising
    providing the tubular member as the inner tube of the surgical instrument, and
    after the swaging, disposing a cutting implement at the distal end of the tubular member.

22. The method of claim 21 further comprising disposing the tubular member for rotation within the outer tube of the surgical instrument.

23. The method of claim 15 further comprising providing the tubular member as outer tube of the surgical instrument, and after the swaging, defining a window at the distal end for exposing a cutting implement carried by the inner tube.

24. The method of claim 15 further comprising providing a second tubular member to serve as the other one of the inner tube or the outer tube, the second tubular member having an open distal end, and swaging the distal end of the second tubular member closed.

25. The method of claim 15 further comprising conveying the tubular member between stations for performing the swaging, cutting, fusing, and forming, and controlling the conveying and coordinating operation of the stations.

26. A method of making a surgical instrument of the kind that includes an inner tube disposed for movement within an outer tube, comprising providing a tubular member adapted to serve as one of the inner tube or the outer tube, the tubular member having an open distal end, rotary swaging the distal end of the tubular member closed, and forming the closed distal end to a share that substantially matches a shape of another one of the inner tube or the outer tube, wherein portions of the tubes are adapted to interact with each other to perform a surgical operation in response to the movement of the inner tube within the outer tube, wherein the method further comprises forming the closed distal end of the tubular member into a selected shape, and performing said forming by pressing the distal end between a pair of dies that define the selected shape, and wherein pressing comprises hammering.

27. The method of claim 26, comprising hydraulically hammering the closed distal end.

28. A method of making a surgical instrument of the kind that includes an inner tube disposed for movement within an outer tube, comprising providing a tubular member adapted to serve as one of the inner tube or the outer tube, the tubular member having an open distal end, swaging the distal end of the tubular member closed, and forming the closed distal end to a shape that substantially matches a shape of another one of the inner tube or the outer tube, wherein portions of the tubes are adapted to interact with each other to perform a surgical operation in response to the movement of the inner tube within the outer tube, the swaging produces a seam in material of the tubular member at the distal end, and further comprising fusing the material together at the seam, and the swaging produces a protrusion of the tubular member material at the seam, and further comprising cutting away a selected amount of the protrusion prior to performing the fusing.

29. A method of making a surgical instrument of the kind that includes an inner tube disposed for movement within an outer tube, comprising providing a tubular member adapted to serve as one of the inner tube or the outer tube, the tubular member having an open distal end, swaging the distal end of the tubular member closed, forming the closed distal end to a shape that substantially matches a shape of another one of the inner tube or the outer tube, wherein portions of the tubes are adapted to interact with each other to perform a surgical operation in response to the movement of the inner tube within the outer tube, and forming the closed distal end of the tubular member into a selected shape, said forming performed by pressing the distal end between a pair of dies that define the selected shape, wherein pressing comprises hammering.

30. The method of claim 29, comprising hydraulically hammering the closed distal end.

* * * * *